US 7,437,192 B2
Oct. 14, 2008

(12) United States Patent
Gill et al.

(54) SYSTEM AND METHOD FOR DETECTING HEART FAILURE AND PULMONARY EDEMA BASED ON VENTRICULAR END-DIASTOLIC PRESSURE USING AN IMPLANTABLE MEDICAL DEVICE

(75) Inventors: Jong Gill, Valencia, CA (US); Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 157 days.

(21) Appl. No.: 11/100,008

(22) Filed: Apr. 5, 2005

(65) Prior Publication Data

US 2006/0224190 A1 Oct. 5, 2006

(51) Int. Cl.
*A61N 1/365* (2006.01)
(52) U.S. Cl. .................................................. 607/23
(58) Field of Classification Search ............ 607/23
See application file for complete search history.

(56) References Cited

U.S. PATENT DOCUMENTS

| | | | | |
|---|---|---|---|---|
| 4,707,481 A * | 11/1987 | Amschler et al. | ............ | 514/247 |
| 5,153,178 A * | 10/1992 | Maroko | ........................ | 514/26 |
| 5,163,429 A | 11/1992 | Cohen | | |
| 5,328,460 A | 7/1994 | Lord et al. | .................... | 604/67 |
| 5,626,623 A | 5/1997 | Kieval et al. | | |
| 5,817,135 A | 10/1998 | Cooper et al. | .................. | 607/17 |
| 5,861,008 A | 1/1999 | Obel et al. | ..................... | 607/11 |
| 6,044,297 A | 3/2000 | Sheldon et al. | ............... | 607/17 |
| 6,277,078 B1 | 8/2001 | Porat et al. | .................. | 600/486 |
| 6,314,323 B1 | 11/2001 | Ekwall | ........................ | 607/23 |
| 6,438,408 B1 | 8/2002 | Mulligan et al. | ............ | 600/510 |
| 6,494,832 B1 * | 12/2002 | Feldman et al. | ............. | 600/301 |
| 6,512,952 B2 | 1/2003 | Stahmann et al. | .............. | 607/9 |
| 6,580,946 B2 | 6/2003 | Struble | ........................ | 607/23 |
| 6,622,045 B2 | 9/2003 | Snell et al. | ..................... | 607/30 |
| 6,628,988 B2 | 9/2003 | Kramer et al. | ................. | 607/9 |
| 6,643,546 B2 | 11/2003 | Mathis et al. | .................. | 607/9 |

(Continued)

FOREIGN PATENT DOCUMENTS

EP 0532148 B1 6/1996

(Continued)

OTHER PUBLICATIONS

Robert M. Berne et al., *Cardiovascular Physiology*, Mosby-Yearbook, Inc., Sixth Edition, p. 69.

(Continued)

*Primary Examiner*—Carl H. Layno
*Assistant Examiner*—Eric D Bertram

(57) ABSTRACT

Techniques are provided for detecting left ventricular end diastolic pressure (LV EDP) using a pressure sensor implanted within the heart of a patient and for detecting and evaluating heart failure and pulmonary edema based on LV EDP. Briefly, the peak of the R-wave of an intracardiac electrogram (IEGM) is used to trigger the measurement of a pressure value within the left ventricle. This pressure value is deemed to be representative of LV EDP. In this manner, LV EDP is easily detected merely by measuring pressure at one point within the heartbeat—thereby eliminating any need to track ventricular pressure throughout the heartbeat. Techniques for detecting and evaluating heart failure and pulmonary edema based on the R-wave triggered LV EDP measurements are also set forth herein.

19 Claims, 9 Drawing Sheets

U.S. PATENT DOCUMENTS

| | | |
|---|---|---|
| 6,666,826 B2 | 12/2003 | Salo et al. .................... 600/485 |
| 2002/0115939 A1 | 8/2002 | Mulligan et al. ............ 600/510 |
| 2002/0120200 A1 | 8/2002 | Brockway et al. ........... 600/488 |
| 2003/0130581 A1 | 7/2003 | Salo et al. .................... 600/485 |
| 2003/0199933 A1 | 10/2003 | Struble |
| 2003/0233118 A1* | 12/2003 | Hui ............................. 606/201 |
| 2004/0049235 A1* | 3/2004 | Deno et al. .................... 607/9 |

FOREIGN PATENT DOCUMENTS

| | | |
|---|---|---|
| WO | WO 01/36014 A2 | 5/2001 |
| WO | WO 01/36014 A3 | 5/2001 |
| WO | WO 02/065894 A2 | 8/2002 |
| WO | WO 02/065894 A3 | 8/2002 |
| WO | WO2004/012808 A1 | 2/2004 |

OTHER PUBLICATIONS

Colucci, Wilson S. et al., "Pathophysiology of Heart Failure", *Heart Disease: A Textbook of Cardiovascular Medicine*, vol. 1, Chapter 16, pp. 503-533.

* cited by examiner

SYSTEM AND METHOD FOR DETECTING HEART FAILURE AND PULMONARY EDEMA BASED ON VENTRICULAR END-DIASTOLIC PRESSURE USING AN IMPLANTABLE MEDICAL DEVICE

FIELD OF THE INVENTION

The invention generally relates to implantable medical devices, such as pacemakers or implantable cardioverter/defibrillators (ICDs), and in particular to techniques for measuring left ventricular end diastolic pressure (LV EDP) and for detecting the onset of heart failure and pulmonary edema based on LV EDP within a patient in which a medical device is implanted.

BACKGROUND OF THE INVENTION

Heart failure is a debilitating disease in which abnormal function of the heart leads in the direction of inadequate blood flow to fulfill the needs of the tissues and organs of the body. Typically, the heart loses propulsive power because the cardiac muscle loses capacity to stretch and contract. Often, the ventricles do not adequately eject or fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles (particularly the left ventricle) to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output. A particularly severe form of heart failure is congestive heart failure (CHF) wherein the weak pumping of the heart leads to build-up of fluids in the lungs and other organs and tissues.

Heart failure has been classified by the New York Heart Association (NYHA) into four classes of progressively worsening symptoms and diminished exercise capacity. Class I corresponds to no limitation wherein ordinary physical activity does not cause undue fatigue, shortness of breath, or palpitation. Class II corresponds to slight limitation of physical activity wherein such patients are comfortable at rest, but wherein ordinary physical activity results in fatigue, shortness of breath, palpitations or angina. Class III corresponds to a marked limitation of physical activity wherein, although patients are comfortable at rest, even less than ordinary activity will lead to symptoms. Class IV corresponds to inability to carry on any physical activity without discomfort, wherein symptoms of heart failure are present even at rest and where increased discomfort is experienced with any physical activity.

The current standard treatment for heart failure is typically centered on medical treatment using angiotensin converting enzyme (ACE) inhibitors, diuretics, beta-blockade, and digitalis. Cardiac resynchronization therapy (CRT) may also be employed, if a bi-ventricular pacing device is implanted. Briefly, CRT seeks to normalize asynchronous cardiac electrical activation and resultant asynchronous contractions associated with CHF by delivering synchronized pacing stimulus to both ventricles. The stimulus is synchronized so as to improve overall cardiac function. This may have the additional beneficial effect of reducing the susceptibility to life-threatening tachyarrhythmias. CRT and related therapies are discussed in, for example, U.S. Pat. No. 6,643,546 to Mathis, et al., entitled "Multi-Electrode Apparatus And Method For Treatment Of Congestive Heart Failure"; U.S. Pat. No. 6,628,988 to Kramer, et al., entitled "Apparatus And Method For Reversal Of Myocardial Remodeling With Electrical Stimulation"; and U.S. Pat. No. 6,512,952 to Stahmann, et al., entitled "Method And Apparatus For Maintaining Synchronized Pacing".

Pulmonary edema is a swelling and/or fluid accumulation in the lungs often caused by heart failure (i.e. the edema represents one of the "congestives" of CHF.) Briefly, the poor cardiac function resulting from heart failure can cause blood to back up in the lungs, thereby increasing blood pressure in the lungs. The increased pressure pushes fluid—but not blood cells—out of the blood vessels and into lung tissue and air sacs. This can cause severe respiratory problems and, left untreated, can be fatal. Pulmonary edema is usually associated with relatively severe forms of heart failure and is often asymptomatic until the edema itself becomes severe, i.e. the patient is unaware of the pulmonary edema until it has progressed to a near fatal state when respiration suddenly becomes quite difficult.

In view of the potential severity of heart failure/pulmonary edema, it is highly desirable to detect the onset of these conditions within a patient and to track the progression thereof so that appropriate therapy can be provided. Many patients suffering heart failure/pulmonary edema already have pacemakers or ICDs implanted therein or are candidates for such devices. Accordingly, it is desirable to provide such devices with the capability to automatically detect and track heart failure/pulmonary edema. Heretofore, a number of attempts have been made to provide for monitoring of physiological parameters associated with heart failure/pulmonary edema using implantable cardiac devices in conjunction with physiological sensors. In particular, it has been recognized that LV EDP often increases due to heart failure or pulmonary edema. (See, for example, discussions of Frank-Starling mechanisms in Braunwald et al., Heart Failure: A Textbook of Cardiovascular Medicine, 6th Ed., Ch. 16, pp. 503-533.) Accordingly, a pressure sensor may be mounted in the left ventricle for directly measuring blood pressure therein. A pacemaker, ICD or other implanted device then receives signals from the pressure sensor, from which it determines LV EDP. Heart failure/pulmonary edema may then be detected and tracked based on LV EDP. See, for example, U.S. Pat. No. 6,438,408 to Mulligan, et al., entitled "Implantable Medical Device For Monitoring Congestive Heart Failure"; U.S. Pat. No. 6,277,078 to Porat, et al., entitled "System and method for monitoring a parameter associated with the performance of a heart"; U.S. Pat. No. 6,666,826 to Salo, et al., entitled "Method and apparatus for measuring left ventricular pressure"; U.S. Pat. No. 6,580,946 to Struble, entitled "Pressure-modulated rate-responsive cardiac pacing"; and U.S. Patent Application 2002/0120200 of Brockway et al., entitled "Devices, Systems and Methods For Endocardial Pressure Measurement."

Heretofore, however, such techniques have met with limited success. A significant problem with techniques for measuring LV EDP using a pressure sensor is that identifying the end diastolic phase of the pressure signal is non-trivial. Typically, pressure signals are generated by the pressure sensor more or less continuously and the implanted device must analyze the signals to identify the end diastolic phase of the heartbeat. This can consume considerable data processing resources within the device itself, which are preferably reserved for other device functions, such as controlling overdrive pacing, CRT pacing, atrial fibrillation (AF) suppression therapy, and the like. FIG. 1 illustrates an exemplary LV pressure profile 2 during a single heartbeat. The end of diastole is identified by vertical line 4. As can be seen, LV pressure increases sharply after the end of diastole. This is due to the closure of the mitral value and subsequent isovolumic contraction of the left ventricle, which increases blood pressure therein, prior to opening of the aortic valve. By continuously monitoring and storing LV pressure signals, the device can detect the sharp increase following closure of the mitral valve, then backtrack through the recorded data to read out the pressure value prior to the increase, i.e. the LV EDP value. This detection processes can consume considerable resources, both in terms of memory and processing time.

Accordingly, it would be highly desirable to provide improved techniques for detecting LV EDP using a pressure sensor, which do not consume significant data processing resources, and it is to that end that the invention is primarily directed. It is also desirable to provide techniques for detecting and tracking heart failure and/or pulmonary edema based on improved LV EDP measurements and other aspects of the invention are directed to that end as well.

SUMMARY OF THE INVENTION

In accordance with the invention, techniques are provided for detecting ventricular EDP using an implantable medical device equipped with at least one cardiac sensing lead and a ventricular pressure sensor. Briefly, an electrical cardiac signal such as an intracardiac electrogram (IEGM) signal is sensed using the lead and the peak amplitude of the signal is identified within a given heartbeat, i.e. the peak of the R-wave associated with the heartbeat is identified. Ventricular EDP is then detected by measuring the pressure within the ventricles using the pressure sensor at a point in time substantially contemporaneous with the peak of the cardiac signal. In other words, detection of the R-wave is used to trigger the measurement of pressure within the ventricles, typically the left ventricle. It is believed that the pressure in the ventricles at the peak of the R-wave is representative of ventricular EDP. In this manner, ventricular EDP is easily detected merely by measuring ventricular pressure at one point within the heartbeat. This eliminates the need to track ventricular pressure throughout the heartbeat and further eliminates the need to analyze the resulting pressure profile in an attempt to identify the point within the profile corresponding to the end of diastole. Hence, data processing and memory resources within the implantable device may be more efficiently used.

Preferably, LV EDP is detected in this manner for each heartbeat, whether paced or sensed. LV EDP is measured for a number of heartbeats over one respiration cycle. The average over one respiration cycle is then used or respiration is tracked and then any changes in LV EDP not caused by respiration are extracted by filtering. The onset of heart failure and/or pulmonary edema may then be detected based on an increase in LV EDP. In one example, heart failure is detected if LV EDP exceeds a first threshold; pulmonary edema is detected if LV EDP exceeds a second, higher threshold. Any subsequent progression of these conditions may be monitored by tracking changes in LV EDP over time. Appropriate warning signals are generated. The warning signals may be delivered directly to the patient using an implanted warning device, if provided, such as a vibrational warning device or a "tickle voltage" warning device. Additionally or alternatively, warning signals may be transmitted to a bedside warning device for display thereon and for forwarding to a physician. Therapy provided by the implanted device may be initiated or adjusted in response to detection of heart failure or pulmonary edema. For example, upon detection of the onset of heart failure, CRT may be activated, assuming it is not already being performed. If an implantable drug pump is provided, appropriate medications may be automatically delivered to address heart failure/pulmonary edema.

Thus, various techniques are provided for use with implantable device for detecting and tracking ventricular EDP based on the timing of R-waves and for also detecting heart failure/pulmonary edema based on changes in ventricular EDP and for triggering appropriate therapy and/or warning signals.

BRIEF DESCRIPTION OF THE DRAWINGS

The above and further features, advantages and benefits of the invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 2:
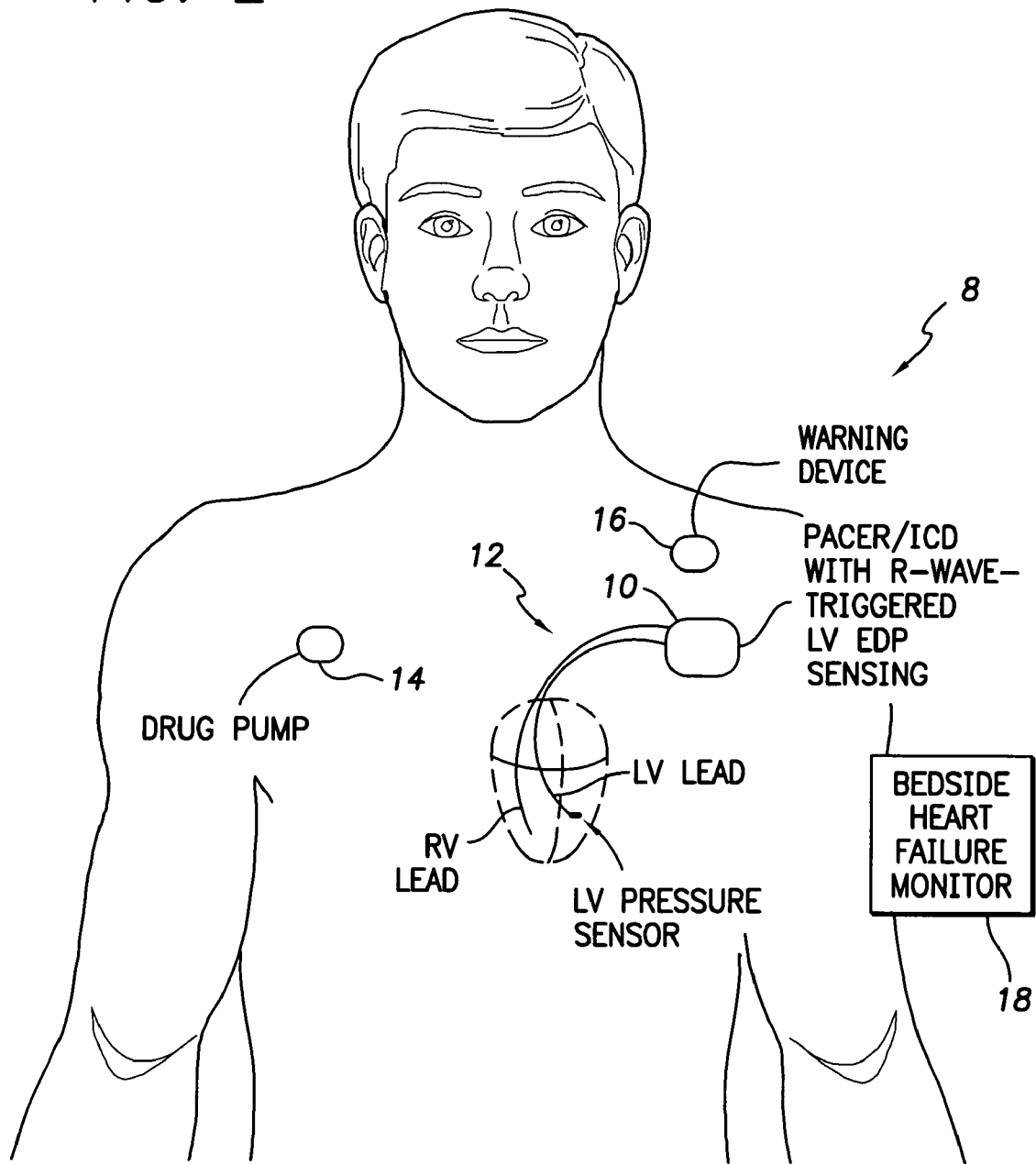
FIG. 2 illustrates pertinent components of an implantable medical system having a pacemaker or ICD capable of detecting and evaluating heart failure/pulmonary edema based on LV EDP measurements.

FIG. 2 illustrates an implantable medical system 8 capable of R-wave triggered LV EDP sensing, i.e. capable of detecting LV EDP by triggering a ventricular pressure sensor to detect pressure during the end diastolic phase of a heartbeat based on R-wave timing. The system is further capable of detecting medical conditions affecting LV EDP, such as heart failure or pulmonary edema, evaluating their severity, tracking their progression and delivering appropriate warnings and therapy. To this end, medical system 8 includes a pacer/ICD 10 or other cardiac stimulation device that incorporates internal components (shown individually in FIG. 9) for controlling LV EDP detection and LV EDP-based heart failure/pulmonary edema evaluation. More specifically, pacer/ICD 10 is equipped to receive signals from cardiac sensing/pacing leads 12 implanted within the heart of the patient from which an IEGM is derived. (In FIG. 2, two leads are shown—an RV lead and an LV lead, in stylized form. A more complete set of leads is set forth in FIG. 8.) A pressure sensor is mounted near a distal end of the LV lead for selectively detecting LV pressure.

In an exemplary technique, described below with reference to FIGS. 3-7, the pacer/ICD detects LV EDP by first detecting the peak of an R-wave portion of a QRS-complex within the IEGM and then activating the pressure sensor at that point in time so as to detect the pressure in the left ventricle substantially contemporaneously with the R-wave. In other words, the pacer/ICD exploits the fact that the R-wave is generally synchronized with the end of diastole. LV EDP values detected in this manner are tracked over time by the pacer/ICD and heart failure and/or pulmonary edema are detected based on significant increases in LV EDP so that appropriate therapy and warnings can be provided. The pacer/ICD also evaluates the severity of the heart failure/pulmonary edema to, for example, identify the particular NYHA class of heart failure and further tracks the progression of heart failure/pulmonary edema based on any changes over time occurring in LV EDP. Additionally, the pacer/ICD performs a wide variety of pacing and/or defibrillation functions such as delivering pacing is response to an arrhythmia or generating and delivering defibrillation shocks in response to fibrillation.

If heart failure and/or pulmonary edema is detected, then appropriate therapy is automatically delivered by the pacer/ICD. For example, once heart failure/pulmonary edema has been detected, CRT therapy may be applied using the leads implanted in the ventricles so as to improve cardiac function. Control parameters for CRT therapy may be automatically adjusted based on the severity of the heart failure/pulmonary edema. Additionally, or in the alternative, the implantable system may be equipped with a drug pump 14 capable of the delivering drug therapy in an attempt to address heart failure/pulmonary edema. Discussions of possible medications for use in heart failure/pulmonary edema patients are provided below. Drug dosages provided by an implantable drug pump may be titrated based on the severity of heart failure/pulmonary edema.

Also, if heart failure and/or pulmonary edema is detected, warning signals are generated using either an internal warning device 16 or an external bedside heart failure monitor 18 to warn the patient of the onset of the condition and to advise of any significant progression thereof. Internal warning device 16 may be a vibrating device or a "tickle" voltage device that, in either case, provides perceptible stimulation to the patient to alert the patient so that the patient may consult a physician. The bedside monitor may provide audible or visual alarm signals to alert the patient, as well as any appropriate textual or graphic displays. In addition, diagnostic information pertaining to LV EDP and to any medical conditions detected thereby may be stored within the pacer/ICD for subsequent transmission to an external programmer (not shown in FIG. 2) for review by a physician during a follow-up session between patient and physician. The physician then prescribes any other appropriate therapies to address the condition. The physician may also adjust the operation of the pacer/ICD to activate, deactivate or otherwise control any therapies that are automatically applied. In addition, the bedside monitor may be directly networked with a centralized computing system for immediately notifying the physician.

Hence, FIG. 2 provides an overview of an implantable system capable of R-wave triggered LV EDP sensing and further capable of detecting and evaluating heart failure/pulmonary edema and delivering appropriate warnings and therapy. Embodiments may be implemented that do not necessarily perform all of these functions. Rather, embodiments may be implemented that provide, for example, only for detecting the onset of heart failure but not pulmonary edema, or vice versa. Other implementations might only provide for tracking the progression of heart failure/pulmonary edema within patients already known to have such conditions. In addition, systems provided in accordance with the invention need not include all the components shown in FIG. 2. In many cases, for example, the implantable system will include only the pacer/ICD and its leads. Drug pumps and warning devices are not necessarily implanted. Some implementations may employ an external monitor for generating warning signals but no internal warning device. These are just a few exemplary embodiments. No attempt is made herein to describe all possible combinations of components that may be provided in accordance with the general principles of the invention. Also, note that, internal signal transmission lines provided for interconnecting the various implanted components are not shown in FIG. 2. Wireless signal transmission may alternatively be employed. In addition, the particular shape, size and locations of the implanted components shown in FIG. 2 are merely illustrative and may not necessarily correspond to actual implant locations. In particular, preferred implant locations for the leads are more precisely illustrated in FIG. 8

R-Wave-Triggered LV EDP Detection Technique

Figure 1:
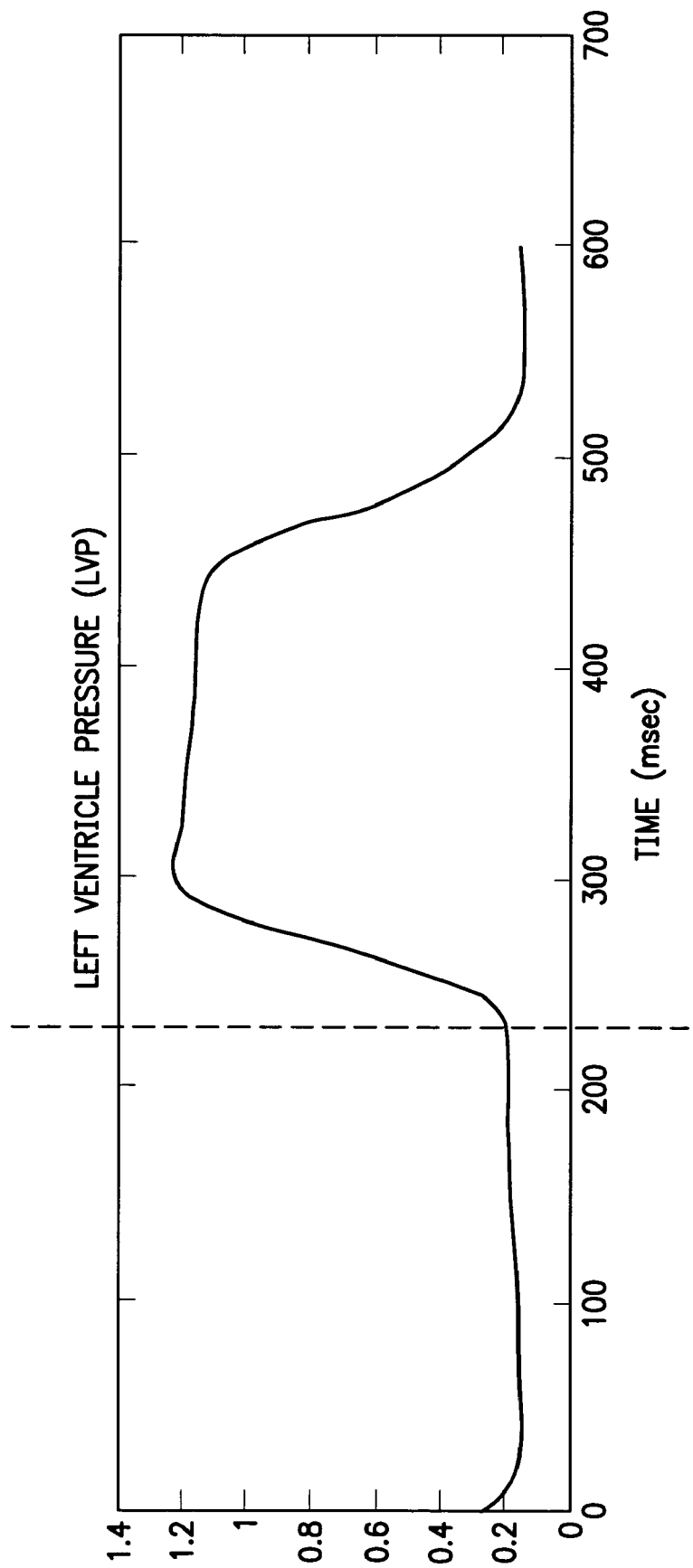
FIG. 1 is a graph illustrating an LV pressure profile of a single heartbeat and particularly identifying the end of diastole within the LV pressure profile.
Figure 3:
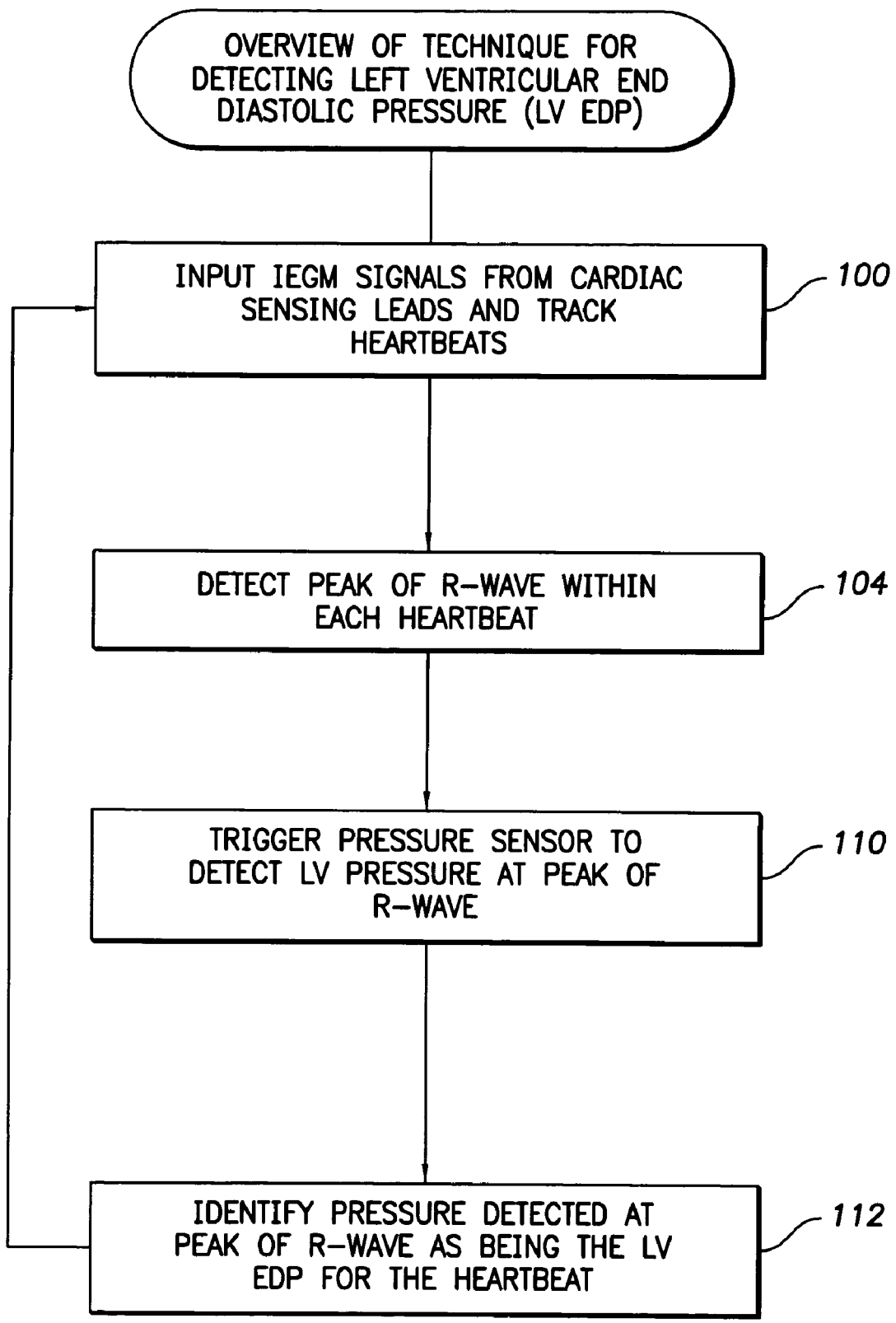
FIG. 3 is a flowchart providing an overview of an R-wave-triggered method for detecting LV EDP as performed by the system of FIG. 2.
Figure 4:
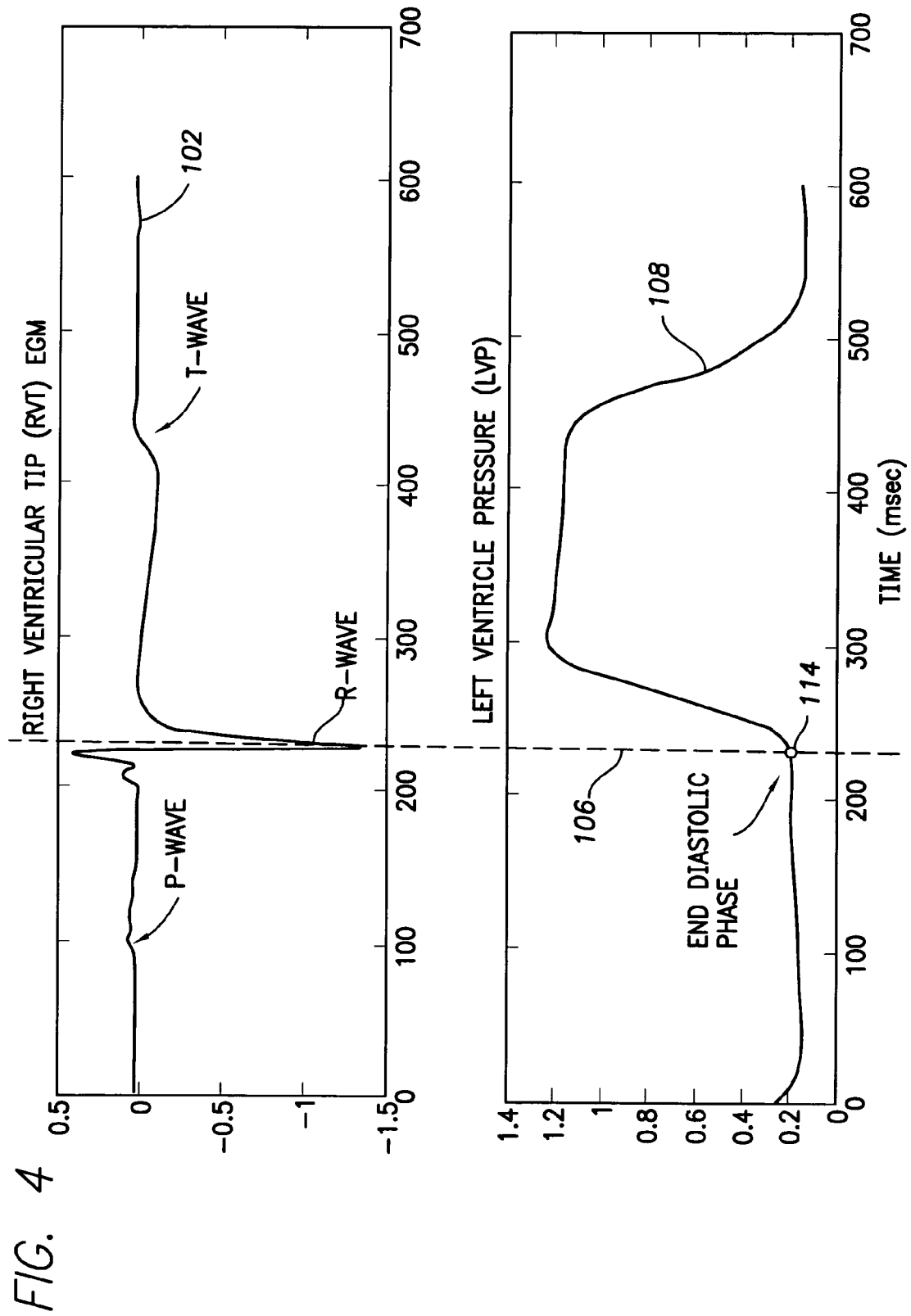
FIG. 4 is a graph illustrating an LV pressure profile and an IEGM profile for a single heart beat and particularly illustrating the synchronization of an R-wave within the IEGM with the end diastolic phase of the LV pressure profile exploited by the measurement technique of FIG. 3.

FIGS. 3 and 4 summarize the detection of LV EDP using a pressure sensor measurements synchronized to the R-wave, which may be performed by the system of FIG. 2. Beginning at step 100, IEGM signals are input from cardiac sensing leads and individual heartbeats are identified based upon P-waves, R-waves and T-waves within the IEGM signals in accordance with otherwise conventional techniques. Strictly speaking, P-waves, R-waves and T-waves are features of a surface electrocardiogram EKG. For convenience, the terms are also used herein to refer to corresponding features of the IEGM. In particular, the peak of a QRS-complex of the IEGM corresponds to the R-wave of the EKG. An exemplary IEGM signal 102 corresponding to a single heartbeat is shown in FIG. 4, with the P-wave, R-wave and T-wave identified. The IEGM signal is sensed by leads implanted with the heart, such as by sensing voltage differences between tips of the LV and RV leads of FIG. 1.

At step 104, the peak of the R-wave within a given heartbeat is detected based upon signal amplitude, i.e. the largest amplitude spike within the IEGM signal for the heartbeat is identified as the R-wave. Within FIG. 4, the peak of the R-wave is denoted by vertical dashed line 106. As can be seen, the peak of the R-wave occurs just prior to a sharp increase in LV pressure, as illustrated by pressure profile 108. As already noted, the sharp increase in LV pressure is due to isovolumic contraction of the left ventricle, which increases blood pressure in the left ventricle, prior to the opening of the aortic valve. The R-wave occurs just prior to the sharp increase in pressure, at least during normal sinus rhythm, because it is the electrical depolarization of myocardial tissue associated with the R-wave that triggers the contraction of the ventricles resulting in the increase in pressure. Typically, there is a slight delay between the electrical depolarization itself and the subsequent increase in ventricular pressure since it takes time for the myocardial tissue of the ventricles to begin to contract in response to the electrical stimulation. In any case, the period of time just prior to the sharp increase in the ventricular pressure represents the end diastolic phase. Hence, the R-wave generally coincides with the end of diastole, at least during normal sinus rhythm. Note that, although the traces of FIG. 4 merely represent data for one exemplary heartbeat, the synchronization illustrated therein between the R-wave and the end of diastole is generally representative of the synchronization occurring during typical heartbeats, at least of those associated with normal sinus rhythm.

Once the peak of the R-wave has been detected, then, at step 110, an LV pressure sensor is triggered to detect pressure in the left ventricle at a point in time substantially contemporaneous with the peak of the R-wave. Pressure sensors for use in the ventricles are described in U.S. Pat. No. 6,314,323 to Ekwall, entitled "Heart Stimulator Determining Cardiac Output, By Measuring the Systolic Pressure, For Controlling the Stimulation". In FIG. 4, the measured pressure value is denoted by reference numeral 114. Since the pressure sensor is triggered by the R-wave and since the R-wave coincides with the end diastolic phase of heartbeat, the pacer/ICD, at step 112, thereby can identify pressure value 114 as being representative of LV EDP for the heartbeat. There is no need to track pressure throughout the entire heartbeat for the purposes of detecting the end of diastole so that LV EDP may be identified, thus conserving power and further conserving data processing resources and memory resources within the pacer/ICD that would otherwise be devoted to storing and analyzing individual pressure values detected throughout the heartbeat. Note that, in some implementations, it may be desirable to nevertheless keep the pressure sensor active at all times to track pressure throughout each heartbeat for diagnostic purposes or other purposes. In such implementations, the pacer/ICD merely identifies the particular pressure value detected during the peak of the R-wave as being representative of LV EDP. Since the pressure sensor is active at all times, power and memory savings are not necessarily achieved. However, the pacer/ICD still conserves data processing resources that would otherwise be needed to analyze the profile for the purposes of detecting the end diastolic phase.

What have been described thus far are techniques for detecting LV EDP using R-wave triggering. As will be explained, these techniques are advantageously employed in connection with tracking LV EDP for the purposes of detecting the onset of heart failure and/or pulmonary edema. However, the LV EDP values detected using the techniques invention may be employed for other purposes as well. Moreover, the detection of the end diastolic phase of a heartbeat based upon R-wave timing may also be employed for other purposes besides detection of LV EDP and may even be exploited with implantable systems not incorporating an LV pressure sensor. Indeed, general principles invention may be exploited with systems not incorporating pacemakers or ICDs but instead incorporating other implantable medical devices benefiting from detection of the end diastolic phase of the heartbeat of a patient. Finally, whereas an example has been described wherein pressure is detected with the left ventricle at a time contemporaneous with the peak of the R-wave, this need not be the case. Rather, it is sufficient that the pressure be detected during a time substantially contemporaneous with the R-wave, i.e. within a window of time surrounding the R-wave that generally corresponds to the end diastolic phase of the heartbeat. The window may extend, for example, from 20 milliseconds (ms) before the R-wave to 20 ms after the R-wave. To detect pressure just prior to the R-wave, the device may be programmed to track the relative timing between consecutive R-waves so as to predict the timing of the next expected R-wave. As can be appreciated, a wide variety of specific implementations may be developed consistent with the principles of the invention and no attempt is made herein to describe or enumerate all such possible implementations.

Heart Failure/Pulmonary Edema Evaluation Technique

Figure 5:
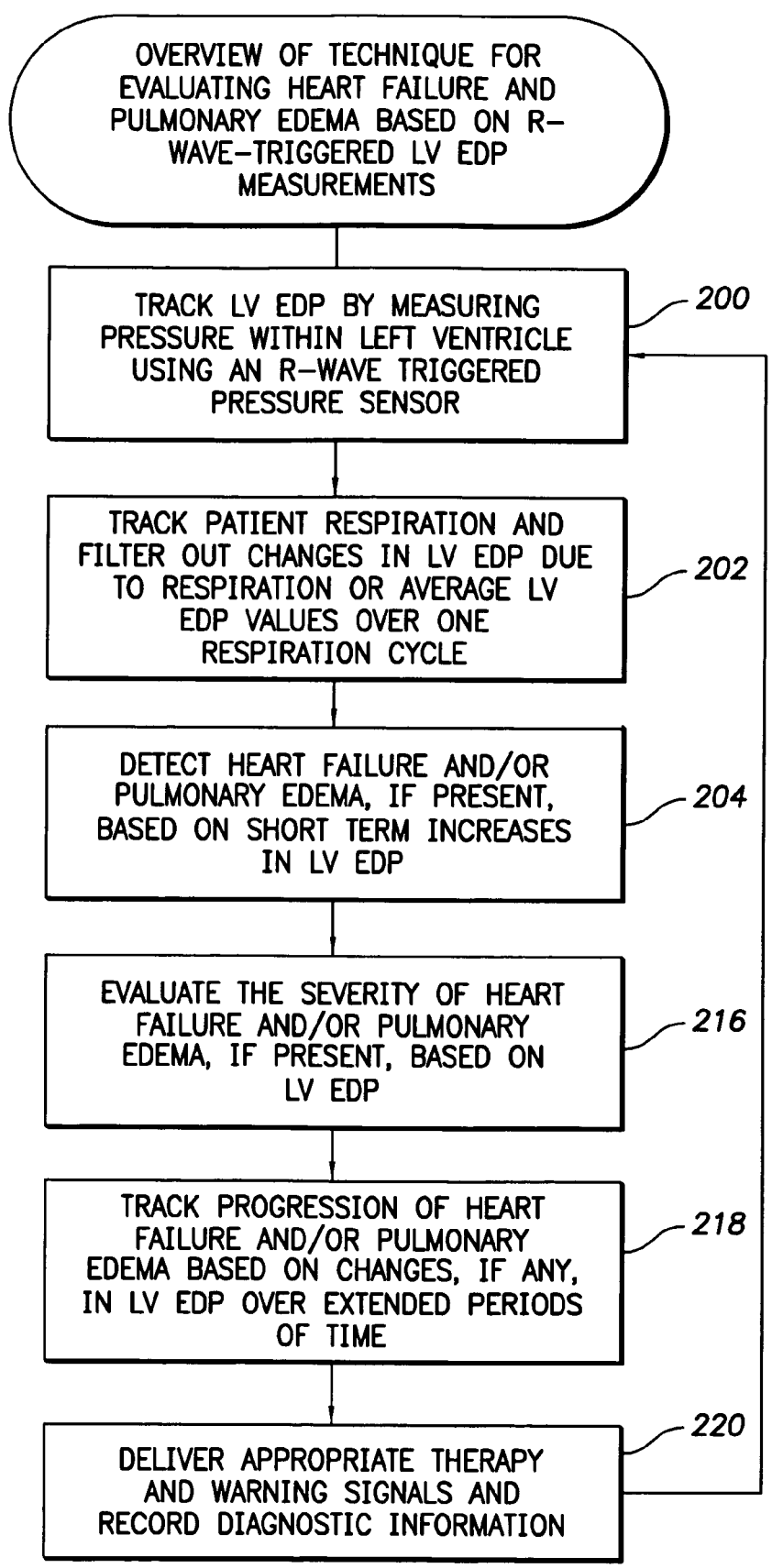
FIG. 5 is a flowchart providing an overview of a technique for detecting and tracking heart failure/pulmonary edema using R-wave-triggered LV EDP values as performed by the system of FIG. 2.
Figure 6:
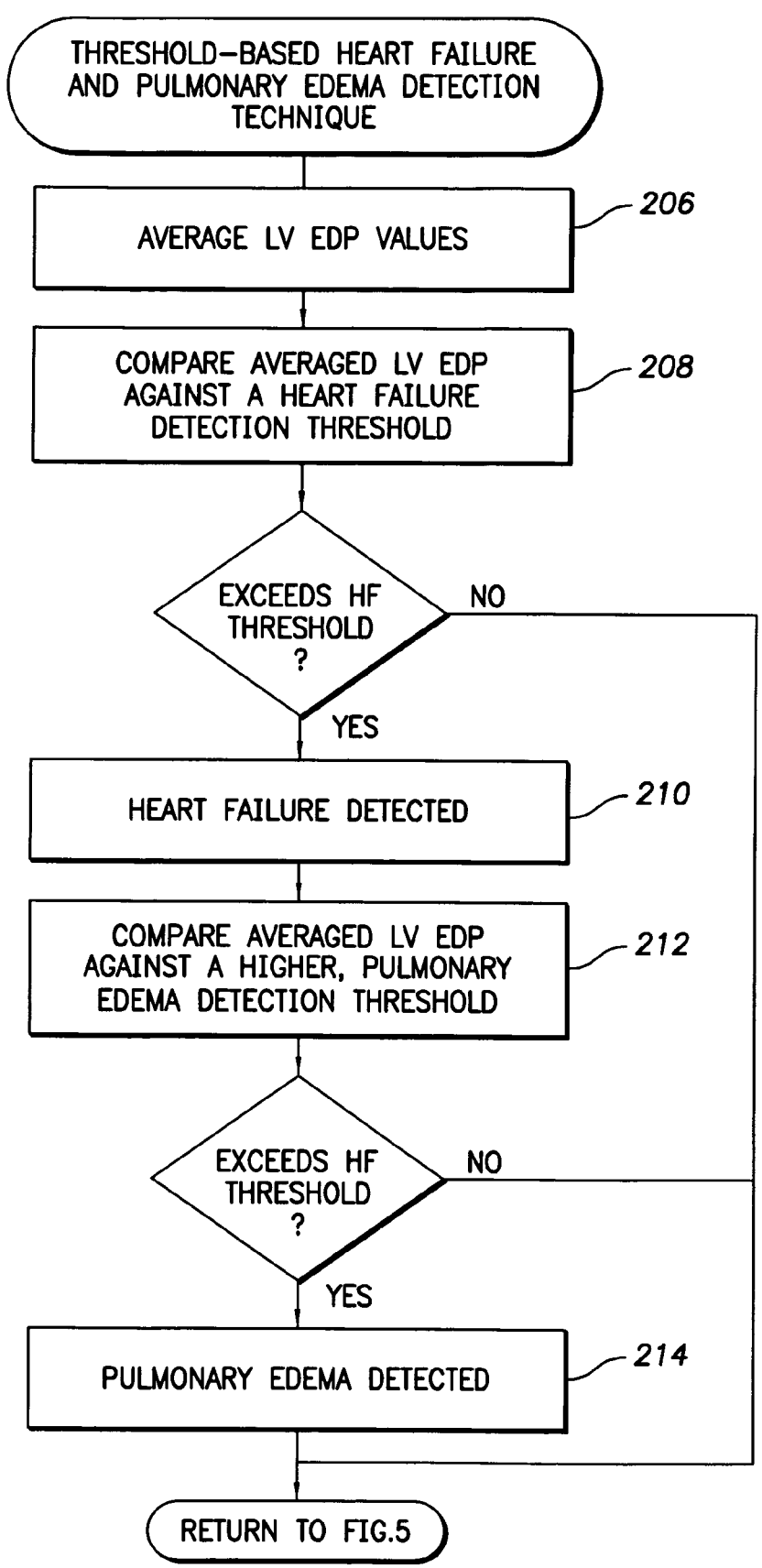
FIG. 6 is a flowchart providing an overview of a threshold-based technique for detecting the onset of heart failure and/or pulmonary edema for use with the technique of FIG. 5.

FIG. 5 summarizes heart failure/pulmonary edema evaluation techniques of the invention that may be performed by the system of FIG. 2 based upon LV EDP values detected using R-wave triggering. At step 200, the implantable pacer/ICD detects LV EDP within the patient by measuring LV pressure using a pressure sensor activated at times synchronized with the peaks of R-waves, in accordance with the techniques described above. At step 202, the pacer/ICD averages LV EDP over all heart beats during one respiration cycle or tracks patient respiration by, for example, tracking changes in thoracic impedance and then filters changes in LV EDP due to respiration from changes due to other factors, such as onset of heart failure. Thoracic impedance may be detected using any of a variety of otherwise conventional techniques. Techniques for detecting impedance are set forth in, e.g., U.S. Pat. No. 5,817,135 to Cooper, et al. entitled, "Rate-Responsive Pacemaker with Noise-Rejecting Minute Volume Determination" and U.S. Pat. No. 5,861,008 to Obel, et al., entitled "Heart Stimulating Device with Stimulation Energy Responsive to Detected Noise".

By filtering out respiration, small changes in LV EDP over time can be more reliably detected. Depending upon the implementation, it may also be desirable to remove possible changes in LV EDP due to other factors, such as patient motion or posture. Patient movement can be tracked using an accelerometer in accordance with well-known techniques. Techniques for detecting patient posture or changes in posture are set forth in U.S. patent application Ser. No. 10/329, 233, of Koh et al., entitled "System and Method for Determining Patient Posture Based On 3-D Trajectory Using an Implantable Medical Device", filed Dec. 23, 2002, which is incorporated by reference herein. Other techniques are set forth in U.S. Pat. No. 6,044,297 to Sheldon, et al. "Posture and Device Orientation and Calibration for Implantable Medical Devices."

It may also be desirable to restrict the periods of time during which LV EDP values are detected to improve LV EDP-based detection of heart failure and pulmonary edema. For example, LV EDP may be detected only when the heart rate of the patient is within a certain predetermined range to reduce any variations in LV EDP caused by excessively high or low heart rates. In addition, the device may be configured to detect LV EDP values only during periods of time when R-R intervals are substantially uniform and when no arrhythmias are occurring so that cardiac rhythm abnormalities caused by an on-going arrhythmia do not adversely affect the evaluation of LV EDP. Alternatively, LV EDP may be detected only, for example, while the patient is at rest or sleeping. As can be appreciated, a wide variety of techniques may be employed for isolating particular circumstances for detecting LV EDP values for use in evaluating heart failure and pulmonary edema. Routine experimentation may be employed to identify particular circumstances that are most effective for use in detecting and averaging LV EDP values so that heart failure and/or pulmonary edema may be most reliably tracked.

At step 204, the pacer/ICD analyzes the LV EDP values to detect heart failure and/or pulmonary edema, if present, based on LV EDP. In one example, set forth in FIG. 6, threshold-based techniques are employed. Briefly, at step 206 of FIG. 6, the pacer/ICD averages values for LV EDP over some predetermined number of heartbeats or some predetermined period of time, such as one day, as specified by device programming, so as to generate a suitable averaged value for use in tracking small changes in LV EDP over time. At step 208, the pacer/ICD then compares the averaged LV EDP against a predetermined heart failure detection threshold. If it does not exceed the threshold, processing returns FIG. 5 for continued monitoring of LV EDP values. If, however, the averaged LV EDP value exceeds the threshold, the onset of heart failure is thereby detected, step 210. Preferably, the detection of heart failure requires that the average LV EDP consistently exceed the threshold over an extended period time, such as days or a week, so that an indication of heart failure is not improperly generated due to transient events occurring within the patient. The threshold may be a preprogrammed value set by the physician during device programming or may be an internally generated value set relative to a baseline LV EDP detected for the patient. The baseline may be, for example, set to the average LV EDP level of patient at the time of implant or may be set based upon a long-term running average of LV EDP. In one specific example, the threshold is set to an LV EDP value 10%-20% (or >20 mmHg) above the baseline value. As an alternative, detection of heart failure may be made based on some combination of LV EDP values and other parameters detected for the patient. For example, if a sensor is provided for evaluating stroke volume, a detection of heart failure is only made if high LV EDP values are corroborated by detection of relatively low stroke volume. Trans-thoracic impedance, exercise trends, etc. can also be used to corroborate the determination made based on LV EDP.

Assuming that the onset of heart failure is detected at step 210 based on elevated LV EDP values, the pacer/ICD continues to determine whether the LV EDP values are additionally indicative of pulmonary edema. Accordingly, at step 212, the pacer/ICD then compares the averaged LV EDP against a predetermined pulmonary edema detection threshold, set to a value higher than the heart failure threshold. If it does not exceed the higher threshold, processing immediately returns to FIG. 5 to respond to the detection of heart failure. If, however, the averaged LV EDP value exceeds the pulmonary edema threshold, the onset of pulmonary edema is thereby also detected, step 214. As with the heart failure threshold, the pulmonary edema threshold may also be a preprogrammed value set, for example, by the physician during device programming or may be an internally generated value set relative to a baseline LV EDP detected for the patient. For example, the pulmonary edema threshold may be set to an LV EDP value 25%-35% (or >30 mmHg) above the baseline LV EDP for the patient.

Processing then returns to FIG. 5 wherein, at step 216, the pacer/ICD evaluates the severity of heart failure and/or pulmonary edema (assuming such condition has been detected), again based on LV EDP values. The severity of heart failure may be evaluated by comparing LV EDP against a table of values representative of various levels of severity of heart failure, such as those set forth in the NYHA classification scheme. In one example, assuming the patient does not have heart failure at the time of implant, the physician determines the initial baseline LV EDP for the patient, then the device sets various severity threshold values based on that baseline value. In any case, at step 218, the pacer/ICD tracks the progression of heart failure and/or pulmonary edema based on changes, if any, in the LV EDP values over time. In this regard, the pacer/ICD stores LV EDP values for the patient for comparison against subsequently detected values to permit tracking of the progression of heart failure and pulmonary edema. For example, LV EDP values may be calculated and stored daily so that any changes day to day can be detected and appropriate diagnostic data stored. Insofar as progression tracking is concerned, the device need only compare the LV EDP values for the patient detected at various baseline times and compare the values against any predetermined threshold values. Depending upon the implementation, the pacer/ICD may be provided only with the progression tracking capability. This may be appropriate, for example, for use in patients who are already known to have heart failure or pulmonary edema so that detection of the onset of the condition is not necessary. At step 220, appropriate therapy and warning signals are delivered and diagnostic data is recorded. As already explained, various types of therapy may be delivered, alone or in combination, depending upon the capabilities of the implanted system.

Figure 7:
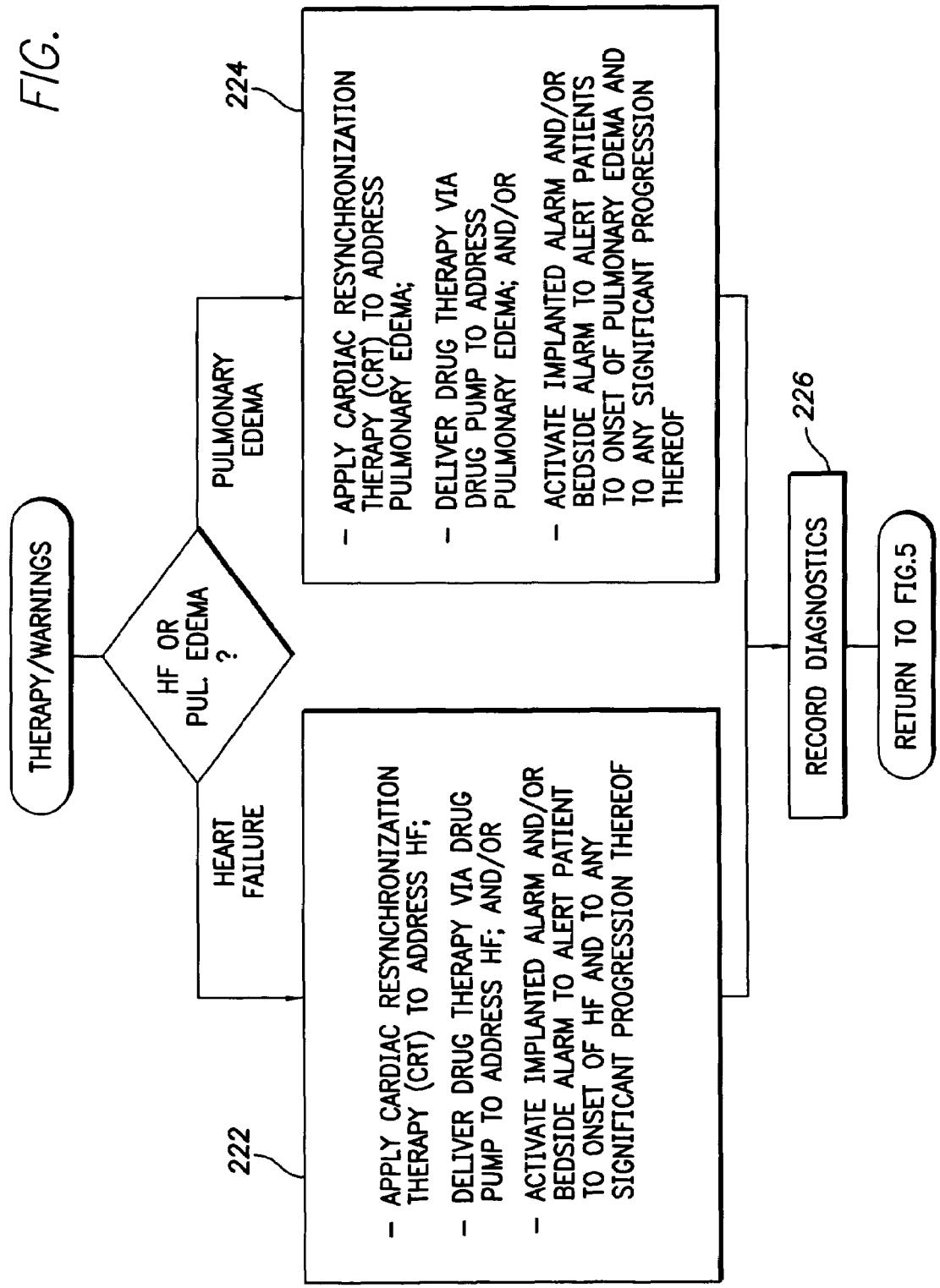
FIG. 7 is a flowchart illustrating therapy performed in accordance with the technique of FIG. 5.

Referring now to FIG. 7, therapy and warning signal generation, activated at step 220 of FIG. 5, will be summarized. Therapy depends on whether heart failure is detected or pulmonary edema. If heart failure, then at step 222, CRT therapy is activated to address heart failure and/or drug therapy specific to heart failure is delivered to the patient. CRT and related therapies are discussed in the above-referenced patents to Mathis, et al., Kramer, et al., and Stahmann, et al. The degree of severity of heart failure may be used to control CRT pacing parameters such as the time delay between left and right ventricular pulses to, for example, provide more aggressive CRT for more severe heart failure. Drug therapy is delivered using an implanted drug pump, if so equipped. Exemplary heart failure medications include ACE inhibitors, diuretics, digitalis and compounds such as captopril, enalapril, lisinopril and quinapril. Depending upon the particular medication, alternative compounds may be required for use in connection with an implantable drug pump. Routine experimentation may be employed to identify medications for treatment of heart failure that are safe and effective for use in connection with an implantable drug pump. Dosages may be titrated based upon the severity of heart failure. Implantable drug pumps are discussed in U.S. Pat. No. 5,328,460 to Lord, et al., entitled "Implantable Medication Infusion Pump Including Self-Contained Acoustic Fault Detection Apparatus".

Warning signals are generated using an implanted warning device, if so equipped, and/or using a bedside monitor. In particular, warnings are generated to alert the patient to the onset of heart failure and to subsequently warn of any significant progression in heart failure. The bedside monitor may be directly networked with a centralized computing system for forwarding any warning signals to the patient's physician. A system incorporating bedside monitoring units connected to a centralized external programmer system is described in U.S. Pat. No. 6,622,045 to Snell et al., "System and Method for Remote Programming of Implantable Cardiac Stimulation Devices." The aforementioned patent to Lord et al. discusses implantable "tickle" warning devices that may be used to deliver internal warning signals.

If pulmonary edema, then, at step 224, CRT therapy is activated to address pulmonary edema, and/or drug therapy specific to pulmonary edema is delivered to the patient. The degree of severity of pulmonary edema may be used to control CRT pacing parameters. Drug therapy response to pulmonary edema may be delivered using the implanted drug pump. Exemplary pulmonary edema medications include diuretics such as furosemide. Assuming that pulmonary edema is caused by heart failure, the aforementioned heart failure medications may be appropriate as well. Again, depending upon the particular medication, alternative compounds may be required for use in connection with an implantable drug pump and routine experimentation may be employed to identify medications for treatment of pulmonary edema that are safe and effective for use in connection with an implantable drug pump. Dosages may be titrated based upon the severity of pulmonary edema. Warning signals specific to pulmonary edema are generated using the implanted warning device and/or bedside monitor.

At step 226, appropriate diagnostic information is stored within the memory 294 (FIG. 5) of the device for subsequent transmission to external programmer during a follow-up session with the patient for review by a physician or for immediate transmission via the bedside monitor to the centralized computing system, if one is provided.

Thus, FIGS. 3-7 provide an overview of the LV EDP detection techniques of the invention and the LV EDP-based heart failure/pulmonary edema detection and evaluation techniques of the invention. In the following section, an exemplary pacer/ICD will be described, which includes components for performing the above-described detection and evaluation techniques.

Exemplary Pacer/ICD

Figure 8:
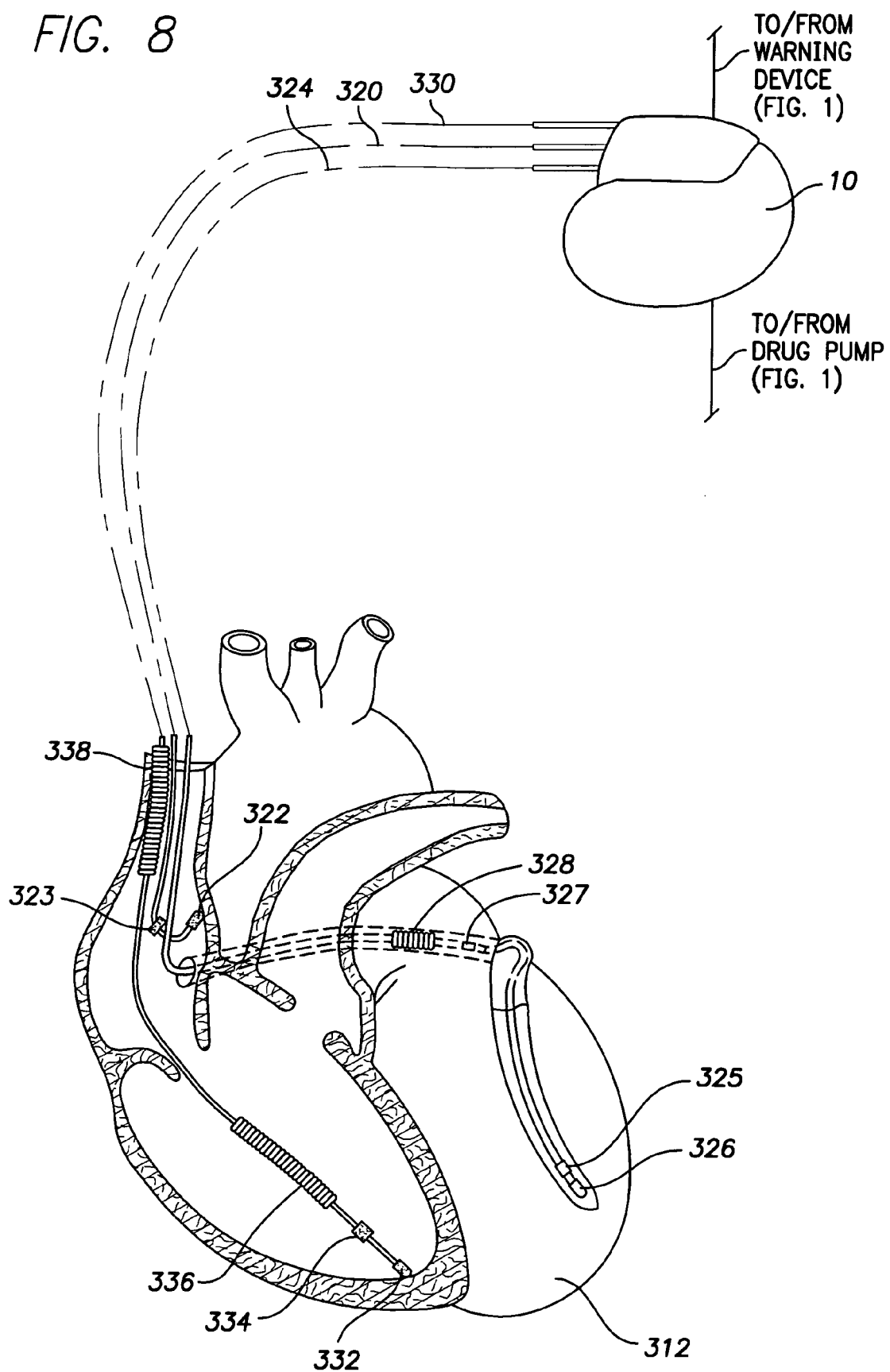
FIG. 8 is a simplified, partly cutaway view, illustrating the pacer/ICD of FIG. 2 along with at full set of leads implanted into the heart of the patient.

FIG. 8 provides a simplified block diagram of the pacer/ICD, which is a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. To provide atrial chamber pacing stimulation and sensing, pacer/ICD 10 is shown in electrical communication with a heart 312 by way of a left atrial lead 320 having an atrial tip electrode 322 and an atrial ring electrode 323 implanted in the atrial appendage. Pacer/ICD 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. Typically, the right ventricular lead 330 is transvenously inserted into the heart so as to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 324 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 324 is designed to receive atrial and ventricular cardiac signals and to deliver left ventricular pacing therapy using at least a left ventricular tip electrode 326, left atrial pacing therapy using at least a left atrial ring electrode 327, and shocking therapy using at least a left atrial coil electrode 328. With this configuration, biventricular pacing can be performed. Although only three leads are shown in FIG. 8, it should also be understood that additional stimulation leads (with one or more pacing, sensing and/or shocking electrodes) may be used in order to efficiently and effectively provide pacing stimulation to the left side of the heart or atrial cardioversion and/or defibrillation. The CS lead also includes a pressure sensor 325 near its distal end for directly sensing LV pressure.

While in certain embodiments pressure sensor 325 is either placed inside the left ventricle, or in a coronary vein overlying the left ventricle, it will be understood by those skilled in the art that pressure sensor may also be placed in other locations. For example, pressure sensor 325 may be placed within the left atrium, since a pressure signal from the left atrium is a surrogate for left ventricular pressure. In this example, the pressure sensor may be located on the end of a lead (as shown in FIG. 8), and the lead may be advanced through the right atrium and through an opening made in the atrial septum and into the left atrium. An example of a left atrial pressure sensor is shown in U.S. patent application Ser. No. 11/053,374, filed Feb. 7, 2005, and assigned to the assignee of the rights in the instant invention, the disclosure of which is hereby expressly incorporated herein by reference.

Figure 9:
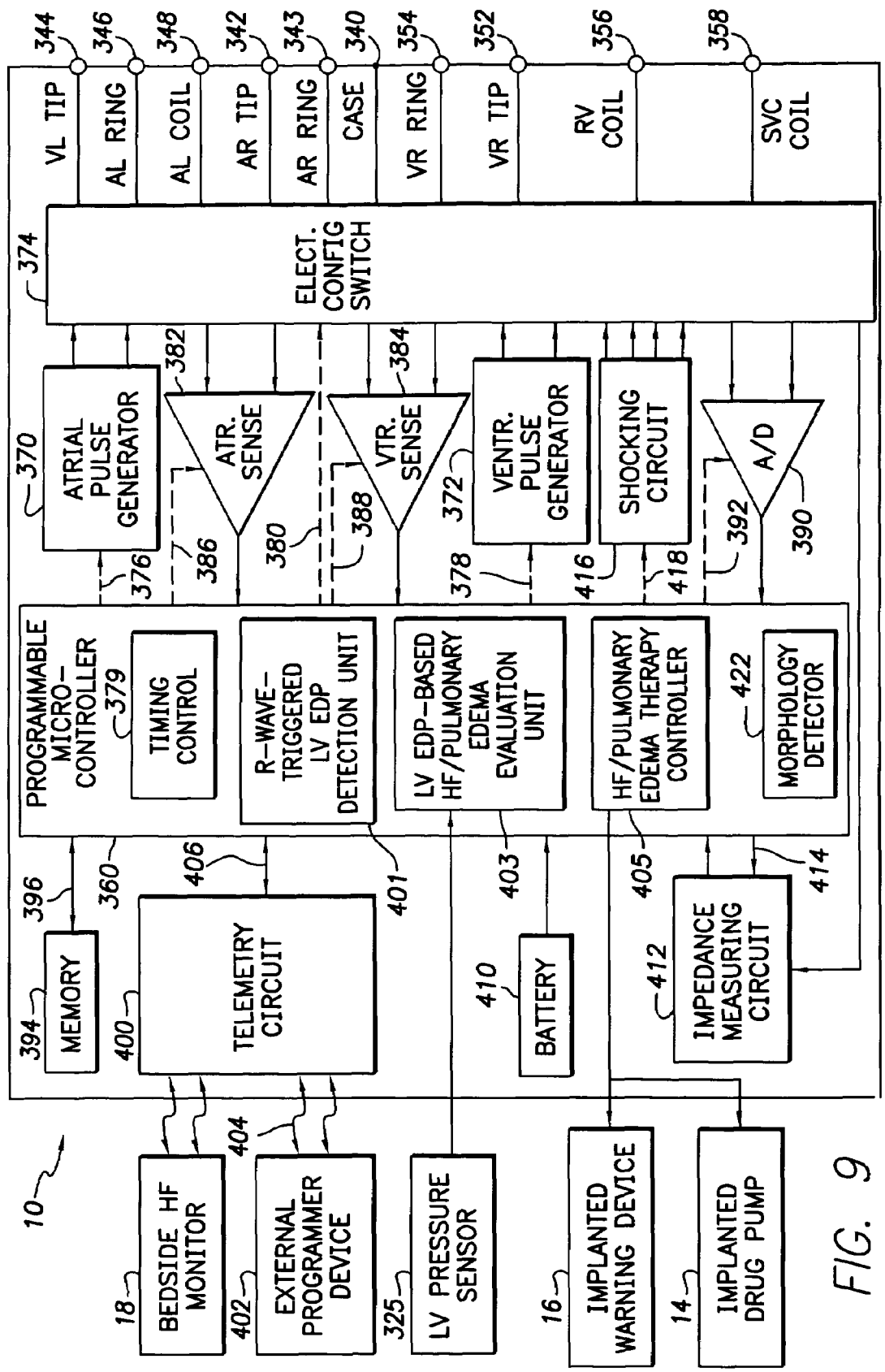
FIG. 9 is a functional block diagram of the pacer/ICD of FIG. 8, illustrating basic circuit elements that provide cardioversion, defibrillation and/or pacing stimulation in the heart and particularly illustrating components for detecting LV EDP using the techniques of FIG. 3, tracking heart failure/pulmonary edema using the techniques of FIGS. 5-6 and controlling delivery of therapy or warning signals in response thereto using the techniques of FIG. 7.

A simplified block diagram of internal components of pacer/ICD 10 is shown in FIG. 9. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 340 for pacer/ICD 10, shown schematically in FIG. 9, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 further includes a connector (not shown) having a plurality of terminals, 342, 343, 344, 346, 348, 352, 354, 356 and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 322 and a right atrial ring ($A_R$ RING) electrode 343 adapted for connection to right atrial ring electrode 323. To achieve left chamber sensing, pacing and shocking, the connector includes at least a left ventricular tip terminal ($V_L$ TIP) 344, a left atrial ring terminal ($A_L$ RING) 346, and a left atrial shocking terminal ($A_L$ COIL) 348, which are adapted for connection to the left ventricular ring electrode 326, the left atrial tip electrode 327, and the left atrial coil electrode 328, respectively. To support right chamber sensing, pacing and shocking, the connector further includes a right ventricular tip terminal ($V_R$ TIP) 352, a right ventricular ring terminal ($V_R$ RING) 354, a right ventricular shocking terminal ($R_V$ COIL) 356, and an SVC shocking terminal (SVC COIL) 358, which are adapted for connection to the right ventricular tip electrode 332, right ventricular ring electrode 334, the RV coil electrode 336, and the SVC coil electrode 338, respectively.

At the core of pacer/ICD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

As shown in FIG. 9, an atrial pulse generator 370 and a ventricular/impedance pulse generator 372 generate pacing stimulation pulses for delivery by the right atrial lead 320, the right ventricular lead 330, and/or the coronary sinus lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 360 via appropriate control signals, 376 and 378, respectively, to trigger or inhibit the stimulation pulses.

The microcontroller 360 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art.

Atrial sensing circuits 382 and ventricular sensing circuits 384 may also be selectively coupled to the right atrial lead 320, coronary sinus lead 324, and the right ventricular lead 330, through the switch 374 for detecting the presence of cardiac activity in each of the four chambers of the heart. Accordingly, the atrial (ATR. SENSE) and ventricular (VTR. SENSE) sensing circuits, 382 and 384, may include dedicated sense amplifiers, multiplexed amplifiers or shared amplifiers.

The switch 374 determines the "sensing polarity" of the cardiac signal by selectively closing the appropriate switches, as is also known in the art. In this way, the clinician may program the sensing polarity independent of the stimulation polarity. Each sensing circuit, 382 and 384, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 382 and 384, are connected to the microcontroller 360 which, in turn, are able to trigger or inhibit the atrial and ventricular pulse generators, 370 and 372, respectively, in a demand fashion in response to the absence or presence of cardiac activity in the appropriate chambers of the heart.

For arrhythmia detection, pacer/ICD 10 utilizes the atrial and ventricular sensing circuits, 382 and 384, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 390. The data acquisition system 390 is configured to acquire intracardiac electrogram signals, convert the raw analog data into a digital signal, and store the digital signals for later processing and/or telemetric transmission to an external device 402. The data acquisition system 390 is coupled to the right atrial lead 320, the coronary sinus lead 324, and the right ventricular lead 330 through the switch 374 to sample cardiac signals across any pair of desired electrodes. The microcontroller 360 is further coupled to a memory 394 by a suitable data/address bus 396, wherein the programmable operating parameters used by the microcontroller 360 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 394 through a telemetry circuit 400 in telemetric communication with the external device 402, such as a programmer, transtelephonic transceiver or a diagnostic system analyzer. The telemetry circuit 400 is activated by the microcontroller by a control signal 406. The telemetry circuit 400 advantageously allows intracardiac electrograms and status information relating to the operation of pacer/ICD 10 (as contained in the microcontroller 360 or memory 394) to be sent to the external device 402 through an established communication link 404. Pacer/ICD 10 further includes an accelerometer or other physiologic sensor 408, commonly referred to as a "rate-responsive" sensor because it is typically used to adjust pacing stimulation rate according to the exercise state of the patient. However, the physiological sensor 408 may further be used to detect changes in cardiac output, changes in the physiological condition of the heart, or diurnal changes in activity (e.g., detecting sleep and wake states) and to detect arousal from sleep. Accordingly, the microcontroller 360 responds by adjusting the various pacing parameters (such as rate, AV Delay, V-V Delay, etc.) at which the atrial and ventricular pulse generators, 370 and 372, generate stimulation pulses. While shown as being included within pacer/ICD 10, it is to be understood that the physiologic sensor 408 may also be external to pacer/ICD 10, yet still be implanted within or carried by the patient. A common type of rate responsive sensor is an activity sensor incorporating an accelerometer or a piezoelectric crystal, which is mounted within the housing 340 of pacer/ICD 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient an, in particular, is capable of detecting arousal from sleep or other movement.

The pacer/ICD additionally includes a battery 410, which provides operating power to all of the circuits shown in FIG. 9. The battery 410 may vary depending on the capabilities of pacer/ICD 10. If the system only provides low voltage therapy, a lithium iodine or lithium copper fluoride cell may be utilized. For pacer/ICD 10, which employs shocking therapy, the battery 410 must be capable of operating at low current drains for long periods, and then be capable of providing high-current pulses (for capacitor charging) when the patient requires a shock pulse. The battery 410 must also have a predictable discharge characteristic so that elective replacement time can be detected. Accordingly, pacer/ICD 10 is preferably capable of high voltage therapy and appropriate batteries.

As further shown in FIG. 9, pacer/ICD 10 is shown as having an impedance measuring circuit 412 which is enabled by the microcontroller 360 via a control signal 414. Herein, impedance is primarily detected for use in evaluating respiration. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 412 is advantageously coupled to the switch 374 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules), as controlled by the microcontroller 360. Such shocking pulses are applied to the heart of the patient through at least two shocking electrodes, and as shown in this embodiment, selected from the left atrial coil electrode 328, the RV coil electrode 336, and/or the SVC coil electrode 338. The housing 340 may act as an active electrode in combination with the RV electrode 336, or as part of a split electrical vector using the SVC coil electrode 338 or the left atrial coil electrode 328 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 360 is capable of controlling the synchronous or asynchronous delivery of the shocking pulses.

Microcontroller 360 also includes various components directed to the controlling the detection of LV EDP and the detection and treatment of heart failure and/or pulmonary edema based on LV EDP. More specifically, for the purposes of detecting LV EDP, the microcontroller includes an R-wave-triggered LV EDP detection unit 401 configured to implement the detection techniques of FIG. 3. An LV EDP-based heart failure/pulmonary edema evaluation unit 403 performs the techniques of FIGS. 5-6 for detecting and evaluating heart failure and/or pulmonary edema. The microcontroller also includes a heart failure/pulmonary edema therapy controller 405, which controls the delivery of therapy and warning signals using techniques summarized in FIG. 7. Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller.

What have been described are various systems and methods for use with a pacer/ICD for detecting LV EDP, for detecting and evaluating heart failure and/or pulmonary edema based on LV EDP, and for providing therapy and warning signals. However, principles of the invention may be exploiting using other implantable systems or in accordance with other techniques. Thus, while the invention has been described with reference to particular exemplary embodiments, modifications can be made thereto without departing from the spirit and scope of the invention.

What is claimed is:

1. A method for detecting ventricular end diastolic pressure (EDP) within a patient having an implantable medical device equipped with at least one electrical cardiac sensing lead and a pressure sensor, the method comprising:

detecting a peak amplitude within an electrical cardiac signal sensed during a heartbeat using the lead;

detecting a value representative of ventricular EDP for the heartbeat using the pressure sensor by triggering the measurement of left ventricular pressure in response to the detection of the peak amplitude within the electrical cardiac signal;

tracking respiration cycles;

tracking heart beats;

averaging ventricular EDP over heart beats during one respiration cycle;

identifying changes in averaged ventricular EDP due to respiration; and detecting changes, if any, in averaged ventricular EDP not due to respiration.

2. The method of claim 1 wherein the peak amplitude detected during the heartbeat is the peak of an R-wave portion of a ORS-complex of the heartbeat.

3. The method of claim 1 wherein the pressure is measured at a time within a detection window surrounding the peak of the electrical cardiac signal, the window extending throughout the end diastolic phase of the heartbeat.

4. The method of claim 1 further comprising tracking changes in ventricular EDP over time.

5. The method of claim 4 wherein tracking changes in ventricular EDP over time comprises tracking ventricular EDP over a plurality of heartbeats.

6. The method of claim 4 further comprising detecting the onset of a selected medical condition within the patient based on changes in ventricular EDP overtime.

7. The method of claim 6 wherein the medical condition is any condition associated with a detectable change in ventricular EDP over time.

8. The method of claim 6 wherein detecting the onset of a selected medical condition is performed by determining whether an increase in LV EDP exceeds a heart failure detection threshold.

9. The method of claim 6 wherein detecting the onset of a selected medical condition is performed by determining whether an increase in LV EDP exceeds a pulmonary edema detection threshold.

10. The method of claim 6 further comprising delivering therapy in response to the medical condition.

11. The method of claim 10 wherein delivering therapy comprises delivering cardiac resynchronization therapy (CRT).

12. The method of claim 10 wherein the device is equipped with an implantable drug pump and wherein delivering therapy comprises delivering selected medications to the patient using the drug pump.

13. The method of claim 6 further comprising generating a warning signal in response to the medical condition.

14. The method of claim 6 wherein detecting the onset of the medical condition is performed by an external programmer device based on signals received from the implanted device.

15. The method of claim 6 further comprising evaluating the severity of the medical condition based on the values representative of LV EDP.

16. The method of claim 15 further comprising tracking changes, if any, in the severity of the medical condition within the patient based on any changes over time in the values representative of LV EDP.

17. A method for detecting the onset of a medical condition within a patient having an implantable medical device equipped with at least one electrical cardiac sensing lead and a pressure sensor, the method comprising:

detecting peak amplitudes within electrical cardiac signals sensed during each of a plurality of heartbeats using the lead;

detecting a value representative of ventricular end diastolic pressure (EDP) for each of the heartbeats using the pressure sensor by triggering a measurement of left ventricular pressure in response to the detection of the peak amplitude of the electrical cardiac signal within the heartbeat;

detecting the onset of selected medical conditions within the patient based on changes in ventricular EDP over time;

averaging ventricular EDP over heart beats during one respiration cycle;

identifying changes in averaged ventricular EDP due to respiration; and detecting changes, if any, in averaged ventricular EDP not due to respiration.

18. A system for detecting ventricular end diastolic pressure (EDP) within a patient having an implantable medical device equipped with at least one electrical cardiac sensing lead and a pressure sensor, the system comprising:

an R-wave detection unit operative to detect a peak amplitude within an electrical cardiac signal sensed during a heartbeat using the lead;

an R-wave-triggered detection unit operative to detect a value representative of ventricular EDP for the heartbeat using the pressure sensor by triggering a measurement of left ventricular pressure in response to the detection of the peak amplitude of the electrical cardiac signal means for averaging ventricular EDP over heart beats during one respiration cycle;

means for identifying changes in averaged ventricular EDP due to respiration; and means for detecting changes, if any, in averaged ventricular EDP not due to respiration.

19. A system for detecting ventricular end diastolic pressure (EDP) within a patient having an implantable medical device equipped with at least one electrical cardiac sensing lead and a pressure sensor, the system comprising:

means for detecting a peak amplitude within an electrical cardiac signal sensed during a heartbeat using the leads;

means for detecting a value representative of ventricular EDP for the heartbeat using the pressure sensor by triggering a measurement of measuring left ventricular pressure in response to the detection of the peak amplitude of the electrical cardiac signal;

means for averaging ventricular EDP over heart beats during one respiration cycle;

means for identifying changes in averaged ventricular EDP due to respiration; and means for detecting changes, if any, in averaged ventricular EDP not due to respiration.

* * * * *